United States Patent [19]
Henry et al.

[11] 3,993,643
[45] Nov. 23, 1976

[54] N-SUBSTITUTED 2-[2-(5-NITRO-2-FURYL) VINYL]IMIDAZOLES

[75] Inventors: David W. Henry, Menlo Park; Michael Cory, Palo Alto, both of Calif.

[73] Assignee: Stanford Research Institute, Menlo Park, Pa.

[22] Filed: May 7, 1976

[21] Appl. No.: 684,289

[52] U.S. Cl. .................. 260/240 A; 260/240.1; 260/309; 424/273
[51] Int. Cl.² .................................. C07D 405/06
[58] Field of Search .............. 260/240 A, 240.1, 309

[56] References Cited
FOREIGN PATENTS OR APPLICATIONS
4,710,878  3/1972  Japan
4,211,829  7/1969  Japan OTHER PUBLICATIONS
Fujita et al., J. Pharm. Soc. Japan, 86, 1966, pp. 427–432.

Henry et al., J. Med. Chem., 16, 1973, pp. 1287–1291.

*Primary Examiner*—Arthur P. Demers
*Attorney, Agent, or Firm*—Donovan J. De Witt

[57] ABSTRACT

N-substituted 2-[2-(5-nitro-2-furyl)vinyl]imidazoles having the structure

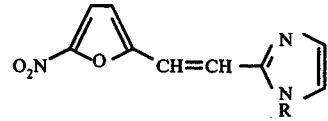

wherein R represents mono- or dimethoxybenzyl, pyridylmethyl, N,N-dimethylaminobenzyl or phenoxypropyl. A preferred compound is 1-(4-methoxybenzyl)-2-[2-(5-nitro-2-furyl)vinyl]imidazole. The compounds have utility as antischistosomal chemotherapeutic agents.

9 Claims, No Drawings

N-SUBSTITUTED 2-[2-(5-NITRO-2-FURYL) VINYL]IMIDAZOLES

ORIGIN OF INVENTION

The invention described herein was made in the course of work under a grant or award from the National Institute of Health, Department of Health, Education, and Welfare.

BACKGROUND OF THE INVENTION

The article, "Chemotherapeutic Nitroheterocycles. Antischistosomal Properties of Nitrofurylvinyl and Nitrothienylvinyl Heterocycles", by D. W. Henry, V. H. Brown, M. Cory and J. G. Johansson, Journal of Medicinal Chemistry, pp 1287–1291, Vol. 16, No. 11 (1973), discloses the preparation of two 2-[2-(5-nitro-2-furyl)-vinyl]imidazole compounds, namely 2-[2-(5-nitro-2-furyl)vinyl]imidazole (which is employed as a starting material for the compounds of this invention) and 1-acetyl-2-[2-(5-nitro-2-furyl)vinyl]imidazole. These compounds are disclosed as having a measure of antischistosomal activity.

Japanese Pat. No. 7,210,878, dated March 31, 1972, discloses the compound wherein R, as employed herein, is benzyl. This compound is described as having utility as a microbicide.

SUMMARY OF INVENTION

The present invention relates to novel N-substituted 2-[2-(5-nitro-2-furyl)vinyl]imidazoles having the structure

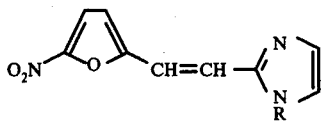

wherein R represents a radical selected from the group consisting of methoxybenzyl, dimethoxybenzyl, pyridylmethyl, N,N-dimethylaminobenzyl or phenoxypropyl.

Representative compounds of the invention include
1-(2,3-dimethoxybenzyl)-2-[2-(5-nitro-2-furyl)vinyl-]imidazole,
1-(3,4-dimethoxybenzyl)-2-[2-(5-nitro-2-furyl)vinyl-]imidazole,
1-(3-methoxybenzyl)-2-[2-(5-nitro-2-furyl)vinyl-]imidazole,
1-(4-N,N-dimethylaminobenzyl)-2-[2-(5-nitro-2-furyl)vinyl]imidazole,
1-(4-picolyl)-2-[2-(5-nitro-2-furyl)vinyl]imidazole,
1-(2-picolyl)-2-[2-(5-nitro-2-furyl)vinyl]imidazole,
1-(phenoxypropyl)-2-[2-5-nitro-2-furyl)vinyl-]imidazole, and
1-(4-methoxybenzyl)-2-[2-(5-nitro-2-furyl)vinyl-]imidazole.

These and other compounds of the invention are solid materials, principally of yellow-to-orange coloration which have well-defined melting points and are soluble in many common organic solvent media.

As will be seen from the examples to follow, which describe the preparation of each of the compounds enumerated above, the compounds of this invention may be prepared by reaction between 2-[2-(5-nitro-2-furyl)vinyl]imidazole and the appropriate halide derivative of the substituent group represented by R. The first-named reactant is prepared by the method described in the above cited Henry et al. paper; for convenience, this preparation is repeated in Example 1.

As will be seen from the tabular data presented following the examples, the novel compounds of this invention have antischistosomal characteristics when administered (usually orally) to mammals. The organism being combated is Schistosoma mansoni and this activity manifests itself by damage to the female worm reproductive system and, in most cases, by killing the worms after the same are formed from the larvae. It is anticipated that with the onset of clinical testing, various of the compounds of this invention will be effective in combating schistosomiasis in man.

DESCRIPTION OF PREFERRED EMBODIMENTS

The present invention is illustrated in various of its embodiments by the following examples, each of which is directed to the preparation of a particular compound of the invention.

EXAMPLE 1

1-(2,3-Dimethoxybenzyl)-2-[2-(5-nitro-2-furyl)vinyl-]imidazole

2-[2-(5-Nitro-2-furyl)vinyl]imidazole. To 14.0 g of 5-nitrofurfural (0.1 mol) was added 8.1 g of 2-methylimidazole (0.1 mol), 80 ml of $Ac_2O$, and 80 ml of AcOH. The solution was stirred at reflux for 4 hr and cooled to 0°. The resulting precipitate was collected and washed with 100 ml of $C_6H_6$. The crude product was recrystallized from EtOAc to give 10.6 g (43%) of red crystals, mp 163°–164°, this representing the compound N-acetyl-2-[2-(5-nitro-2-furyl)vinyl]imidazole. To 2.2 g (0.01 mol) of the latter compound was added 20 ml of 6 N HCl and 10 ml of EtOH. The reaction mixture was stirred at reflux for 1 hr, cooled, and evaporated in vacuo to dryness. The residue was recrystallized from $CH_3CN$ to yield 0.778 g (38%) of yellow crystals, mp 223°.

To a mixture of 3.36 g (20 mmoles) of 2,3-dimethoxybenzyl alcohol in 15 ml of benzene was added 15 ml of concentrated HCl. The reaction mixture was stirred at ambient temperature for 4 hrs. The benzene layer was separated, the aqueous layer was washed with benzene. The combined benzene layers were washed with $H_2O$ followed by saturated $NaHCO_3$ then $H_2O$. The dry benzene ($Na_2SO_4$) was evaporated in vacuo to give 3.5 g of a colorless oil which was dissolved in 15 ml of dry DMF. To this solution was added 5.0 g (36 mmoles) of anhydrous $K_2CO_3$ and 3.0 g (14.5 mmoles) of 2-[2-(5-nitro-2-furyl)vinyl]imidazole prepared as described in the preceding paragraph. The resulting mixture was stored at ambient temperature for 3 days. The resulting mixture was poured into 300 ml of $H_2O$. The precipitated solid was collected and recrystallized from MeOH yielding 1.4 g of yellow crystals, mp 159°–161°, this being the captioned compound.

Anal. Calcd. for $C_{18}H_{17}N_3O_5$: C, 60.84; H, 4.82; N, 11.82. Found: C, 60.57; H, 4.78; N, 11.93.

EXAMPLE 2

1-(3,4-Dimethoxybenzyl)-2-[2-(5-nitro-2-furyl)vinyl-]imidazole

Using the same general procedure as employed in Example 1, the captioned compound was prepared from 3,4-dimethoxybenzyl chloride (as prepared from the corresponding alcohol) in lieu of the 2,3-dimethoxybenzyl chloride intermediate of Example 1.

EXAMPLE 3

1-(3-Methoxybenzyl)-2-[2-(5-nitro-2-furyl)vinyl]imidazole

Using the same general procedure of Example 1, the captioned compound was prepared using 3-methoxybenzyl chloride and 2-[2-(5-nitro-2-furyl)vinyl]imidazole. After recrystallization from ethanol water the product melted at 143°–145°.

Anal. Calcd. for $C_{17}H_{15}N_3O_4 \cdot 0.25H_2O$: C, 61.83; H, 4.74; N, 12.75. Found: C, 62.09; H, 4.49; N, 12.66.

EXAMPLE 4

1-(4-N,N-dimethylaminobenzyl)-2-[2-(5-nitro-2-furyl)vinyl]imidazole

Using the same general procedure of Example 1, the captioned compound was prepared using 4-dimethylaminobenzyl chloride and 2-[2-(5-nitro-2-furyl)vinyl]imidazole. Three recrystallizations from benzene-petroleum ether gave a product, mp 125°–126°.

Anal. Calcd. for $C_{18}H_{18}N_4O_3$: C, 63.89; H, 5.36; N, 16.56. Found: C, 63.94; H, 5.46; N, 16.94.

EXAMPLE 5

1-(4-Picolyl)-2-[2-(5-nitro-2-furyl)vinyl]imidazole

Using the same general procedure of Example 1, the captioned compound was prepared using 4-picolyl chloride and 2-[2-(5-nitro-2-furyl)vinyl]imidazole. Recrystallization from ethanol-water gave an orange solid product melted 130°–131°.

Anal. Calcd. for $C_{15}H_{12}N_4O_3 \cdot 0.5H_2O$: C, 59.0; H, 4.29; N, 18.4. Found: C, 59.1; H, 4.08; N, 18.2.

EXAMPLE 6

1-(2-Picolyl)-2-[2-(5-nitro-2-furyl)vinyl]imidazole

Using the same general procedure of Example 1, the captioned compound was prepared using 2-picolyl chloride and 2-[2-(5-nitro-2-furyl)vinyl]imidazole. The resulting yellow product was recrystallized from benzene-petroleum ether and melted at 141°–142°.

Anal. Calcd. for $C_{15}H_{12}N_4O_3$: C, 60.8, H, 4.08; N, 18.9. Found: C, 60.9; H, 3.97; N, 18.68.

EXAMPLE 7

1-(Phenoxypropyl)-2-[2-(5-nitro-2-furyl)vinyl]imidazole

Using the same general procedure of Example 1, the captioned compound was prepared using 3-phenoxypropyl bromide and 2-[2-(5-nitro-2-furyl)vinyl]imidazole. The resulting orange product after recrystallization from ethanol-water melted at 85°–86°.

Anal. Calcd. for $C_{18}H_{17}N_3O_4$: C, 63.7; H, 5.05; N, 12.4. Found: C, 63.6; H, 5.17; N, 12.2.

EXAMPLE 8

1-(4-Methoxybenzyl)-2-[2-(5-nitro-2-furyl)vinyl]imidazole

Using the same general procedure of Example 1, the captioned compound was prepared using 2-[2-(5-nitro-2-furyl)vinyl]imidazole and 4-methoxybenzyl bromide. Recrystallization from benzene-ethanol gave an orange solid, mp 151°–152°.

Anal. Calcd. for $C_{17}H_{15}N_3O_4$: C, 62.8; H, 4.65, N, 12.9. Found: C, 63.0; H, 4.72; N, 12.7.

As indicated above, the compounds of the invention set forth in the examples were prepared in non-salt form inasmuch as they were to be administered orally in the described test program. When the compounds are to be prepared in a water soluble form they can take the form of acid addition salts. This is usually effected by adding anydrous acid to a solution of the active compound in an appropriate organic solvent. The salt is recovered by a practice of conventional solvent evaporation and crystallization techniques. In preparing the compounds in salt form, any pharmaceutically acceptable acid may be employed, such, for example, as hydrochloric acid, sulfuric acid, citric acid or acetic acid.

To evaluate the antischistosomal characteristics of the present compounds in mammals, lots of 10 mice each were given oral dosages (twice a day for three days) of each of the N-substituted 2-[2-(5-nitro-2-furyl)vinyl]imidazole compounds of Examples 1 through 8, the mice so treated having been infected 6 weeks earlier with larvae of Schistosoma mansoni. The dosage level (mg/kg of body weight) for each compound employed is given in the table presented below. Half of the mice were sacrificed at the end of two days following the termination of the dosage program, and these mice were examined to provide a variety of data including that showing the percent of mice exhibiting harm to the female worm reproductive system, said value also being expressed in the table. The balance of the mice were sacrificed at the end of a five-week term following treatment and a count was made of the number of worms per animal. A count was also made of the number of worms per animal in a controlled lot of mice which have been infected with Schistosoma mansoni but had not been dosed with any antischistosomal compound. These data are presented in the table, first as the average percent reduction in worm count (as compared to the average number of worms found in the controls) and second as the percent of cured mice, i.e., those which were free of worms.

| ANTISCHISTOSOMAL EFFECT OF N-SUBSTITUTED 2-(5-NITRO-2-FURYL)VINYL IMIDAZOLES | | | | | |
|---|---|---|---|---|---|
| Compound of Example No. | Dose mg/kg b.i.d. | Mouse Mortality (%) | Damage to female worm repro sys (%) | Reduction in worm count (%) | Parasite cures (%) |
| 1 | 100 | 10 | 28 | 0 | 0 |
| 2 | 400 | 0 | 36 | 32 | 0 |
| 3 | 400 | 0 | 23 | 95 | 50 |
| 4 | 400 | 0 | — | 20 | 0 |
| 5 | 350 | 15 | 62 | 79 | 33 |
| 6 | 350 | 15 | 25 | 0 | 0 |
| 7 | 400 | 0 | 42 | 40 | 0 |
| 8 | 550 | 0 | — | 83 | 14 |

What is claimed is:

1. As an antischistosomal agent, a compound having the structure

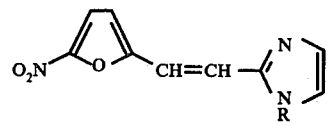

wherein R represents a radical selected from the group consisting of methoxybenzyl, dimethoxybenzyl, pyridylmethyl, N,N-dimethylaminobenzyl and phenoxypropyl, or the pharmaceutically acceptable acid addition salts thereof.

2. The antischistosomal agent of claim 1 which is 1-(2,3-dimethoxybenzyl)-2-(5-nitro-2-furyl)vinyl]imidazole, or the pharmaceutically acceptable acid addition salts thereof.

3. The antischistosomal agent of claim 1 which is 1-(3,4-dimethoxybenzyl)-2-[2-(5-nitro-2-furyl)vinyl]imidazole, or the pharmaceutically acceptable acid addition salts thereof.

4. The antischistosomal agent of claim 1 which is 1-(3-methoxybenzyl)-2-[2-(5-nitro-2-furyl)vinyl]imidazole, or the pharmaceutically acceptable acid addition salts thereof.

5. The antischistosomal agent of claim 1 which is 1-(4-N,N-dimethylaminobenzyl)-2-[2-(5-nitro-2-furyl)vinyl]imidazole, or the pharmaceutically acceptable acid addition salts thereof.

6. The antischistosomal agent of claim 1 which is 1-(4-picolyl)-2-[2-(5-nitro-2-furyl)vinyl]imidazole, or the pharmaceutically acceptable acid addition salts thereof.

7. The antischistosomal agent of claim 1 which is 1-(2-picolyl)-2-[2-(5-nitro-2-furyl)vinyl]imidazole, or the pharmaceutically acceptable acid addition salts thereof.

8. The antischistosomal agent of claim 1 which is 1-(phenoxypropyl)-2-[2-(5-nitro-2-furyl)vinyl]imidazole, or the pharmaceutically acceptable acid addition salts thereof.

9. The antischistosomal agent of claim 1 which is 1-(4-methoxybenzyl)-2-[2-(5-nitro-2-furyl)vinyl]imidazole, or the pharmaceutically acceptable acid addition salts thereof.

* * * * *